(12) United States Patent
Pütter et al.

(10) Patent No.: US 6,909,016 B2
(45) Date of Patent: Jun. 21, 2005

(54) PRODUCTION OF BUTANE TETRACARBOXYLIC ACID DERIVATIVE BY MEANS OF COUPLED ELECTROSYNTHESIS

(75) Inventors: Hermann Pütter, Neustadt (DE); Andreas Weiper-Idelmann, Waldsee (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/432,253

(22) PCT Filed: Nov. 16, 2001

(86) PCT No.: PCT/EP01/13319

§ 371 (c)(1),
(2), (4) Date: May 22, 2003

(87) PCT Pub. No.: WO02/42249

PCT Pub. Date: May 30, 2002

(65) Prior Publication Data

US 2004/0035715 A1 Feb. 26, 2004

(30) Foreign Application Priority Data

Nov. 22, 2000 (DE) .......................................... 100 57 888

(51) Int. Cl.⁷ .............................................. C07C 55/00
(52) U.S. Cl. ...................................... 562/590; 562/592
(58) Field of Search ................................ 562/400, 512, 562/590; 205/440, 415

(56) References Cited

U.S. PATENT DOCUMENTS 6,063,256 A    5/2000   Hannebaum et al.

FOREIGN PATENT DOCUMENTS

| DE | 195 33 773 | 3/1997 |
| DE | 196 18 854 | 11/1997 |
| EP | 0 433 260 | 6/1991 |
| FR | 2 597 509 | 10/1987 |
| JP | 53 101311 | 9/1978 |
| JP | 05 156478 | 6/1993 |

OTHER PUBLICATIONS

W. Li et al.: "Paired electrosynthesis of organic compounds" Electrochemistry, vol. 67, No. 1, pp. 4–10 1998.

Manuel M. Baizer Organic Electrochemistry, pp. 1422–1430 1991.

Elektrochemische Reaktions–Technik Und Synthese, pp. 484–490 and 537–543 1999.

Demetrios Kyriacou Modern Electroorganic Chemistry, chapter 4.2, pp. 169–181 1999.

*Primary Examiner*—Johan Richter
*Assistant Examiner*—Karl J. Puttlitz
(74) *Attorney, Agent, or Firm*—Oblon, Spivak, McClelland, Maier & Neustadt, P.C.

(57) ABSTRACT

A process for preparing butanetetracarboxylic acid derivatives as product of value I by coupled electrosynthesis which comprises cathodically reducing a compound selected from the group consisting of maleic esters, maleic ester derivatives, fumaric esters and fumaric ester derivatives where at least one hydrogen atom in positions 2 and 3 may be replaced by inert groups and obtaining a product of value II at the node.

12 Claims, No Drawings

PRODUCTION OF BUTANE TETRACARBOXYLIC ACID DERIVATIVE BY MEANS OF COUPLED ELECTROSYNTHESIS

The present invention relates to a process for preparing butanetetracarboxylic acid derivatives by coupled electrosynthesis and the use thereof.

Butanetetracarboxylic acid derivatives are very useful as intermediates, for example in the plastics-processing industry. It would accordingly be desirable to have a process whereby butanetetracarboxylic acid derivatives can be prepared in It is similarly desirable that such preparative processes be economical with regard to both natural resources and costs.

Following a long development phase, preparative organic electrochemistry has been one way since about the 1970s to synthesize chemicals in an environmentally friendly and highly selective manner. Hitherto this preparative technique has preferentially been used for the "monosynthesis" of substances either by anodic oxidation or by cathodic reduction. The coproduct produced at the counterelectrode in each case typically has to be separated off and disposed of. Even where this can be done smoothly, the energy invested for the coreaction is wasted. This manifests itself in the high power consumption of such electrochemical monosyntheses, since the coupled reaction does not provide any economic benefit. Furthermore, the by-produced waste materials are responsible for high disposal costs, out of all economic proportion with the recovered product.

A further disadvantage is the inevitable need for a large amount of equipment associated with the use of divided electrolytic cells, since two cell circuits are required and they have to be separated by a membrane or diaphragm. This separation leads to a loss of energy on account of the Ohmic heat produced as a result. To minimize this energy loss, the circuit for the counterelectrode is frequently charged with an aqueous (>80% $H_2O$) conducting salt solution. As a consequence, the cathode product is almost exclusively hydrogen (or the anode product substantially oxygen) which has to be disposed of as a waste product by controlled burning since it is contaminated.

EP-A 0 433 260 discloses an electrochemical process for preparing butanetetracarboxylic esters by monosynthesis. Dialkyl maleates are converted into butanetetracarboxylic esters, which are subsequently hydrolyzed to obtain butanetetracarboxylic acid. This conversion is a cathodic electrodimerization, which is carried out in an undivided electrochemical cell in the presence, inter alia, of an alcohol. The alcohol, generally methanol, is converted at the anode into oxidation products, for example methoxymethanol or methyl formate. Following electrodimerization, the particular butanetetracarboxylic ester has to be separated from the electrolysis solution by crystallization and subsequent filtration and may be hydrolyzed to butanetetracarboxylic acid in a further step in an acidic medium.

One disadvantage of this process is that it is a monosynthesis associated with the above-recited disadvantages for these methods of synthesis, for example the fact that the products formed at the anode in the course of the electrolysis, such as methoxymethanol, have to be disposed of as an unwanted waste product.

Accordingly, it is not just the disposal costs for the waste products, but all the costs due to the equipment, energy and material used to produce just the one product which have to be borne by its commercial utilization, since the products formed concurrently at the anode have hitherto not been commercially utilizable.

As to the possibility of coupling the anode and cathode reactions, there have been repeated suggestions in the literature, for example in M. M. Baizer et al., "Organic Electrochemistry", M. Dekker, New York 1991, pages 1422 ff. or W. Li, T. Nonaka, T.-S. Chou, Electrochemistry 67, 1 (1998), 4–10, that anode and cathode reactions be coupled in such a way that some of the abovementioned disadvantages are avoided. However, the coupled electrosyntheses described therein have further disadvantages, which have generally prevented their scale-up from the laboratory scale to a commercially usable size. For instance, at least one electrode may be poisoned and selectivity decreases over time.

Further disadvantages of these processes are the frequently occurring reactions between the products formed at the electrodes or even between the reactants. This not only greatly reduces the yield of the actual main product by the further, secondary products formed but also greatly compromises the work-up of the reaction solution.

The disadvantages just mentioned frequently lead to cell designs that can be not scaled-up to an industrial scale, or to yields so low that the process is so inefficient that it no longer constitutes an economic advance.

Coupled electrosynthesis has only very recently been successfully used in industry. DE-A 1 196 18 854 discloses a process for preparing phthalide and may be coupled with a multiplicity of anodic oxidations which in turn lead to a further commercially usable product. However, hitherto no further cathodic partner has become known for such an industrially feasible process.

It is therefore an urgent question for sustained development in this art whether there are cathodic reactions, known from the scientific literature, which are likewise impervious to anode processes and so are able to produce the resource requirements of prior art industrially feasible electrosyntheses.

It is an object of the present invention to provide an economical process for preparing butanetetracarboxylic acid derivatives that avoids the disadvantages discussed above.

Surprisingly, it has been found that it is possible to produce butanetetracarboxylic acid by coupling the electrosynthesis thereof at the cathode with suitable processes occurring at the anode. In addition, it has been found that the number of possible coupled partner reactions is surprisingly high.

The objective of the present invention therefore relates to a process for producing butanetetracarboxylic acid as the product of value I by means of coupled electrosynthesis, whereby the compound that is cathodically reduced is selected from the group consisting of maleic esters, maleic ester derivatives, fumaric esters and fumaric ester derivatives where at least one hydrogen atom in positions 2 and 3 may be replaced by inert groups. Simultaneously, a product of value II is obtained at the anode.

Coupled electrosynthesis for the purposes of the present invention is a process for preferably preparing organic products. Its defining feature is that the cathodic reduction to produce a product of value I is coupled with an oxidation at the anode that leads to a product of value II. By virtue of this process, the current input can be used twice. Compared with the hitherto customary monosyntheses of products of value I and II, this leads to an improved economic ratio of total product yield to energy to be expended therefore.

The electrolysis may in general be carried out in divided or undivided cells.

In a preferred embodiment of the present invention, coupled electrosynthesis for preparing butanetetracarboxylic acid derivatives is carried out in an undivided electrochemical cell. This substantially avoids the above-described disadvantages which are common in the case of electrolyses in divided cells.

Useful reactants for synthesizing butanetetracarboxylic acid derivatives by coupled electrosynthesis include in principle all maleic or fumaric esters. Preference is given to using $C_1$–$C_6$-alkyl esters of said acids, particularly preferably dimethyl maleate and dimethyl fumarate.

Useful reactants further include maleic ester or fumaric ester derivatives where at least one hydrogen atom in positions 2 and 3 may be replaced by inert groups. The maleic or fumaric ester derivatives to be used for the purposes of the present invention include for example methyl-, cyano-, hydroxymethyl- and also methoxy-substituted derivatives.

In a further embodiment of the present invention, the maleic ester or fumaric ester derivative is dimethyl maleate or dimethyl fumarate.

Useful electrode materials for the present invention include in principle all common electrode materials for preparative organic electrochemistry.

The reaction may be carried out in divided and undivided cells. It is preferably carried out in undivided cells.

The following equipment variants may be mentioned by way of example:

Undivided cells having a plane-parallel electrode arrangement or candle-shaped electrodes are preferably used in those cases where neither the reactants nor the products which are produced or converted at anode or cathode are adversely affected by whichever is the other electrode process, or react with one another. The electrodes are preferably disposed in a plane-parallel arrangement because this embodiment combines a narrow interelectrode gap (from 0.5 mm to 30 mm, preferably from 1 to 10 mm) with homogeneous current distribution. In this case, the electrodes are preferably employed singly or in stacks of a plurality thereof. In the latter case, the electrodes are stacked electrodes, which may be connected in a bipolar series in a stacked plate cell.

It is also possible to use cells as described in DE-A 195 33 773.

In an illustrative embodiment of the present invention, the electrode material comprises materials based on carbon and/or metallic materials individually or as a mixture of two or more thereof. Preference is given to using electrodes comprising carbon-based materials such as graphite, glassy carbon, graphite felt or electrodes comprising instrument grade graphite.

The electrolytes used in the invention generally comprise the reactants dissolved in a solvent or solvent mixture and also a conducting salt. When the stacked plate cells described in DE-A 195 33 773 are used, the use of conducting salt may be dispensed with by using the cell design described in D. Hoormann et al. GDCh Monograph 14, "Elektrochemische Reaktionstechnik und Synthese" J. Russow, G. Sandstede, R. Staab (ed.) GDCh, 1999, p. 537–543 and V. Kroner et al, ibid., p. 484–490.

In an embodiment of the invention, the total concentration of reactants and products in the electrolyte is in each case in the range from 1 to 70% by weight, preferably in the range from 3 to 50% by weight, particularly preferably in the range from 10 to 40% by weight, subject to the proviso that their sum total should not exceed 75% by weight.

Useful solvents for the reactants used include all solvents customary in organic electrochemistry and also mixtures of two or more thereof.

In a preferred embodiment of the present invention, a solvent or solvent mixture is used in the practice of the process according to the invention in a weight fraction of not less than 50%, preferably not less than 65%, based on the total weight of all the substances used in the process.

In an illustrative embodiment of the present invention, the solvent or solvent mixture used is selected from a group consisting of methanol, ethanol, acetic acid, dimethyl sulfoxide, tetrahydrofuran, dioxane, acetonitrile and mixtures of two or more thereof.

In an embodiment of the present invention, the solvent or solvent mixture is preferably selected from the group consisting of aliphatic $C_1$- to $C_9$-alcohols, preferably $C_1$- to $C_4$-alcohols. But preferably the solvent used is methanol.

In the present invention, the solvent or solvent mixture chosen generally includes less than 10% by weight of water, preferably less than 5% by weight of water, particularly preferably less than 1% by weight of water.

Useful conducting salts of the present invention include all conducting salts useful in preparative electrochemistry or else mixtures of two or more thereof.

Accordingly, in an embodiment of the present invention, the process of the invention is carried out using at least one conducting salt.

This at least one conducting salt is selected from a group consisting of tetraalkylammonium salts, tetrafluoroborates, alkali metal salts, salts of aromatically substituted sulfonic acids, salts of methanesulfonic acid, salts of perchloric acid, bromides, iodides, phosphates, phosphonates, alkoxycarbonates, carboxylates, sulfates, alkylsulfonates and alkyl sulfates, especially acetates and formates and also salts of maleic acid or fumaric acid or monoesters thereof.

The present invention is preferably carried out using a conducting salt comprising salts of methanesulfonic acid and of acetic acid, particular preference being given to salts of methylsulfuric acid.

In the present invention, the at least one conducting salt is used in an amount of from 0.2 to 15% by weight, preferably in an amount of from 0.3 to 5% by weight, particularly preferably in an amount of from 0.4 to 3% by weight, based on the electrolyte.

In a further embodiment, the conducting salt is replaced by an ion exchange membrane.

Generally, coupled electrosynthesis may be carried out at any temperature consistent with the substances used and their solvents. In the present invention, the electrolysis is carried out at temperatures in the range from 0° C. to the boiling point of the particular solvent or solvent mixture used, but preferably at temperatures in the range from 0° to 100° C., particularly preferably at temperatures in the range from 25° to 65° C.

In principle the product of value II prepared in the coupled anodic process can be chosen independently of the cathodically prepared product of value I. This makes it possible to adapt the production flexibly to the commercial demand for the two products of value.

The process of the invention is thus not affected by the otherwise customary disadvantages of coupled processes, for example the rigid quantitative ratio between the two coproducts, which limits commercial flexibility.

The present process of the invention provides as product of value II a product which is not exclusively formed from the solvent.

In a further embodiment of the present invention, product of value II is a product selected from the group consisting of acetals of aromatic aldehydes, methoxylated heterocycles, aromatics and olefins, methoxylated amides, α-hydroxyketals, α-hydroxyacetals, carboxylic acids and carboxylic esters.

Useful anodic coupled reactions surprisingly include substantially all electrochemical oxidations generally known to one skilled in the art, for example the oxidations of C—O or C—N functions. Similarly, the formation of heterocycles, such as the formation of oxazolidinones from the corresponding N-(hydroxyethyl)formamides and also the formation of corresponding six- and seven-membered rings, is useful as anodic coupled reaction. Also useful are many anodic reactions known from organic electrochemistry textbooks, for example D. Kyriakou, Modern Electroorganic Chemistry, Springer, Berlin 1994, section 4.2, such as alkoxylation, acyloxylations and also couplings of olefins such as enol ethers. Similarly, the dimerization of activated —CH compounds or aromatics, such as trimethylbenzene, or the oxidation of amines, alcohols or aromatic systems, for example hydroquinone ethers or heterocycles such as furans, may be chosen as a possible coupled anodic reaction.

Some coupled anodic processes are preferably carried out in the presence of a mediator. Possible coupled anodic processes and their mediatorization are described for example in D. Kyriakou, Modern Electroorganic Chemistry, Springer, Berlin 1994, section 4.2. Useful mediators include in particular halogen compounds, especially bromides or iodides.

It is further possible in the present invention for the reactant used for the anodic preparation of product of value II to react with the at least one solvent, even though the amount of the solvent which is needed for the anodic reaction is substantially removed compared to the anodic monoprocedure by the presence of the cathodic reaction participants.

In a preferred illustrative embodiment of the present invention, the coupled anodic reaction is chosen in such a way that the boiling points of product of value I and product of value II differ by not less than 10° C., so that the two products of value may easily be separated by distillation, for example, in the course of the work-up of the electrolysis solution.

The method of working up the electrolysis solution generally depends on the properties of the resultant products of value I and II. Generally the products of value may be worked up and separated by any work-up methods familiar to one skilled in the art, for example distillation, crystallization or else precipitation reactions.

In the present invention, the butanetetracarboxylic acid derivatives, product of value I, are generally separated from the rest of the electrolysis solution by distillation. It has been determined in this context that, surprisingly, the four carboxylic ester functions of the butanetetracarboxylic acid derivatives prepared according to the invention do not react with the cathodic products even under the thermally drastic conditions of a distillation, even though in general both the ester function of the reactant and the ester function of the product tend to enter such reactions even under electrolytic conditions for example.

In a further embodiment of the present process according to the invention, the solvent or solvent mixture and also all other low-boiling constituents of the electrolysis effluent are distilled off first, and the solvent or solvent mixture may be wholly or partly recycled back into the electrolysis circuit. The remaining mixture, which predominantly includes the two desired products, is subsequently distilled in a distillation column having fewer than 5 theoretical plates to remove one of the products under reduced pressure. Here preference is given to the use of thin-film evaporators and Sambays.

The process of the invention provides the desired butanetetracarboxylic acid commercially useful product of value II without the current efficiency and material yield at the cathode being noticeably impaired as a result.

In principle the process of the invention may be carried out using any divided or undivided electrolytic cell known to one skilled in the art, but it is preferably carried out using an undivided electrolytic cell. The electrolytic cell may also be part of a loop apparatus in which the particular electrolyte used may be recirculated, heated or else cooled. The electrolytic cell construction preferred for the purposes of the present invention is more particularly described in an example recited hereinbelow.

Since the process of the invention has the above-recited advantages such as flexible product coordination, twofold energy utilization, etc. it is preferably suitable for use in the chemical and pharmaceutical industries.

Accordingly, the present invention also provides for the use of the process according to the invention for preparing butanetetracarboxylic acid derivatives as an intermediate for manufacturing drugs, crop protection agents, dyes, complexing agents and also polymer building blocks.

The present invention will now be more particularly described with reference to selected examples.

EXAMPLES

Example 1

Electrolytic Cell

An undivided cell has 11 annular disk electrodes each about 140 cm$^2$ in surface area arranged in the form of a stack. The disks are each about 50 mm in thickness. Spacers are used to space the disks about 1 mm apart, so that there are 10 gaps between the 11 annular disk electrodes. The electrode material used is graphite. The inner disks are connected in a bipolar series during electrolysis. The uppermost annular disk electrode is connected as the anode by means of a graphite plunger and a surface disk. The bottommost electrode is connected as the cathode via the base plate of the electrolytic cell. The particular electrolyte is introduced into the cell through the central base plate and then becomes distributed between uppermost electrode. The cell just described is part of a loop apparatus.

Example 2

Electrolysis of Dimethyl Maleate and p-xylene 2 152 g of dimethyl maleate, 396 g of p-xylene, 209 g of saturated sodium monomethyl sulfate solution and 1 243 g of methanol were electrolyzed in an electrolytic cell described in Example 1 at 48° C. and a current of 5 A. The current decreased from 5 to 3.75 A in the course of the electrolysis. The voltage of the subcells was 6 V throughout the entire electrolysis process. The electrolysis was discontinued after a charge input of 1 F with respect to dimethyl maleate.

The electrolysis effluent contained (determined via GC area percent) methyl butanetetracarboxylate and dimethyl 2-methoxysuccinate at 20% by weight each. p-Xylene and the other two methoxylation products, p-tolyl methyl ether and p-tolylaldehyde dimethyl acetal, as product of value II were present in an amount ratio of 1:1.8:2.4. The p-xylene conversion was more than 85% by weight.

The electrolysis solution was worked up by distillation.

Tetramethyl butanetetracarboxylate was obtained at a yield of 45%, based on the dimethyl maleate used, and in a purity of more than 97%.

The product of value II, p-tolylaldehyde dimethyl acetal, is used, inter alia, as an intermediate for manufacturing, for example, drugs, crop protection agents, UV stabilizers and opacity inhibitors in plastics.

Example 3

Electrolysis of Dimethyl Maleate and Dimethylformamide

An electrolytic cell as described in example 1 was used to electrolyze 600 g of dimethyl maleate, 300 g of dimethylformamide and 15 g of $LiBF_4$ in 2 085 g of methanol at 45° C. under a current of 5 A for a period of 3.35 h. At the end of this period, more than 95% by weight of dimethyl maleate had been converted. The product of value II was N-methoxymethyl-N-methylformamide, formed from dimethylformamide.

Four identical electrolytic batches were run and worked up together by distillation.

Tetramethyl butanetetracarboxylate was obtained in a yield of 60% by weight, based on the dimethyl maleate used, and a purity of greater than 95%.

N-Methoxymethyl-N-methylformamide was obtained in a yield of more than 80% by weight, based on dimethylformamide used. The product is predominantly used in analyses to methoxylate amides. It is further used as a reagent for introducing $N-CH_2$ functions, for example into aromatic systems.

Example 4

Electrolysis of Dimethyl Maleate and Furan

The electrolytic cell in this case featured only 3 gaps of 0.5 mm each. The cathode sides of the graphite electrodes were each provided with a layer of graphite felt (KFD 02, SGL Carbon) 2 mm in thickness.

3 500 g of electrolyte containing 9.4% of furan, 40% of dimethyl maleate, 1% of NaBr and 49.6% of methanol were electrolyzed at 19–24° C. using a current of 5 A until the charge input was 1.1 F with respect to dimethyl maleate (which corresponds to 2.4 F with respect to furan). The effluent contained the products, furan and dimethoxyfurans, in a ratio of 1.0:9.3, which corresponds to a conversion of 90%. The selectivity to dimethoxydihydrofuran/dimethoxytetrahydrofuran was 99%. Dimethyl maleate conversion was more than 99%. Tetramethyl butanetetracarboxylate and dimethyl succinate were formed in a ratio of 1:0.31 and tetramethyl butanetetracarboxylate and methoxysuccinic acid in a ratio of 1:1.15.

Example 5

Electrolysis of Dimethyl Maleate and DMF

A cell as described by L. Kröner et al., GDCh monograph 14, "Elektrochemische Reaktionstechnik und Synthese" J. Russow, G. Sandstede, R. Staab (ed.), GDCh, Frankfurt 1999, pages 484–490, was used. Seven graphite felt annular disks, each 0.61 $dm^2$ in area and 6 mm in thickness, were alternated with 7 Nafion membranes having the same area to form a stack. The uppermost felt disk was connected as the cathode through a graphite disk and the bottom felt disk as the cathode in a corresponding fashion.

The Nafion membranes (Nafion 117, DuPont) were aged in 5% sulfuric acid at 40° C. for 15 h before use.

A batch of 18.2% of DMF, 9.1% of water, 63.6% of methanol and 9.1% of dimethyl maleate was then run at a current of 0.6 A and a temperature of 28–35° C. To convert Nafion membrane from its $H^+$ form into a salt form (here: $Li^+$ form), the electrolyte was admixed with 0.5 ml of an aqueous LiOH solution, the pH of the solution remaining in the neutral range at from 7.0 to 7.5.

The electrolysis was run to a maleic acid conversion of 51%. The dimethyl maleate:butanetetracarboxylic ester GC area ratio in the electrolysis effluent was 1.00:0.70, while the GC area ratio for dimethyl maleate and succinic ester in the electrolysis effluent was 1.00:0.34; methoxysuccinic ester was not formed in a significant amount (>3%).

At the anode, N-methoxymethyl-N-methylformamide was formed at a selectivity of 95%.

We claim:

1. A process for preparing a butanetetracarboxylic acid derivative as product I by coupled electrosynthesis in an electrochemical cell, which comprises (1) cathodically reducing a compound selected from the group consisting of maleic esters, maleic ester derivatives, fumaric esters and fumaric ester derivatives, wherein the maleic ester- and fumaric ester-derivatives are selected from the group consisting of methyl-, cyano-, hydroxymethyl- and methoxy-substituted derivatives, where at least one hydrogen atom in positions 2 and 3 may be replaced by inert groups, and obtaining an isolatable product II at the anode, isolatable wherein the product II is selected from the group consisting of acetals of aromatic aldehydes, methoxylated heterocycles, aromatics and olefins, methoxylated amides, α-hydroxyketals, α-hydroxyacetals, carboxylic acids and carboxylic esters, and wherein the electrode material comprises materials based on carbon, and (2) working up and separating the butane tetracarboxylic acid derivative from the rest of the electrolysis solution.

2. A process as claimed in claim 1, conducted in an undivided electrochemical cell.

3. A process claimed in claim 1, wherein the compound is dimthyl maleate or dimethyl fumarate.

4. A process as claimed in claim 1, wherein a solvent or solvent mixture is used for the implementation of the process in a weight fraction of equal to or not less than 40% based on the total weight of all the substances used in the process.

5. A process as claimed in claim 4, wherein the solvent or solvent mixture used is selected from the group consisting of methanol, ethanol, acetic acid, dimethyl sulfoxide, tetrahydrofuran, dioxane, acetonitrile and mixtures of two or more thereof.

6. A process as claimed in claim 1, wherein at least one conducting salt is used.

7. A process as claimed in claim 6, wherein the at least one conducting salt is selected from the group consisting of tetraalkylammonium salts, tetra-fluoroborates, alkali metal salts, salts of aromatically substituted sulfonic acids, salts of methanesulfonic acid, salts of perchloric acid, bromides, iodides, phosphates, phosphonates, alkoxycarbonates, carboxylates, sulfates, alkylsulfonates and alkyl sulfates.

8. A process as claimed in claim 1, wherein an ion exchange membrane is present in the electrochemical cell.

9. A process as claimed in claim 1, wherein product I differs in boiling point from product II by not less than 10° C.

10. A process as claimed in claim 1, wherein the coupled electrosynthesis includes an anodic reaction of p-xylene.

11. A process as claimed in claim 1, wherein the coupled electrosynthesis includes an anodic reaction of dimethylformamide.

12. A process as claimed in claim 1, wherein the coupled electrosynthesis includes an anodic reaction of furan.

* * * * *